(12) United States Patent
Kirchberger et al.

(10) Patent No.: US 10,596,340 B2
(45) Date of Patent: Mar. 24, 2020

(54) SEAL FORMING STRUCTURE FOR A PATIENT INTERFACE AND A TOOL AND METHOD OF MANUFACTURING THE SEAL FORMING STRUCTURE

(71) Applicant: ResMed Pty Ltd, Bella Vista, New South Wales (AU)

(72) Inventors: Andreas Kirchberger, Miesbach (DE); Johann Sebastian Burz, Germaringen (DE); Bernd Christoph Lang, Graefelfing (DE); Johannes Nickol, Neukenroth (DE); Jens Rothfuss, Munich (DE); Robert Eibl, Bad Toelz (DE); Christian Bayer, Penzberg (DE)

(73) Assignee: ResMed Pty Ltd, Bella Vista (AU)

( * ) Notice: Subject to any disclaimer, the term of this patent is extended or adjusted under 35 U.S.C. 154(b) by 453 days.

(21) Appl. No.: 15/319,222

(22) PCT Filed: Jun. 17, 2015

(86) PCT No.: PCT/EP2015/063660
§ 371 (c)(1),
(2) Date: Dec. 15, 2016

(87) PCT Pub. No.: WO2015/193408
PCT Pub. Date: Dec. 23, 2015

(65) Prior Publication Data
US 2017/0151407 A1    Jun. 1, 2017

(30) Foreign Application Priority Data
Jun. 17, 2014    (EP) ..................................... 14172727

(51) Int. Cl.
*A61M 16/06* (2006.01)
*B29C 43/20* (2006.01)
(Continued)

(52) U.S. Cl.
CPC ........ *A61M 16/0611* (2014.02); *A61M 16/06* (2013.01); *A61M 16/0605* (2014.02);
(Continued)

(58) Field of Classification Search
CPC .... A61M 16/0605–0611; A61M 16/06; A61M 16/0616–0655
See application file for complete search history.

(56) References Cited

U.S. PATENT DOCUMENTS

| 4,782,832 A | 11/1988 | Trimble et al. |
| 4,790,306 A | 12/1988 | Braun et al. |

(Continued)

FOREIGN PATENT DOCUMENTS

| EP | 1 099 452 | 5/2001 |
| EP | 1 946 901 | 7/2008 |

(Continued)

OTHER PUBLICATIONS

International Search Report for PCT/EP2015/063660, dated Sep. 29, 2015, 8 pages.

(Continued)

*Primary Examiner* — Valerie L Woodward
(74) *Attorney, Agent, or Firm* — Nixon & Vanderhye P.C.

(57) ABSTRACT

The technology provides for a cushion assembly or a tool for forming the cushion assembly for a patient interface delivery of a supply of pressurised air or breathable gas to an entrance of a patient's airways. The cushion assembly has an inferior surface and a mask connection portion, and includes a pad arranged on the inferior surface for sealingly contacting a wearer's face in use.

21 Claims, 9 Drawing Sheets

Figure 1:
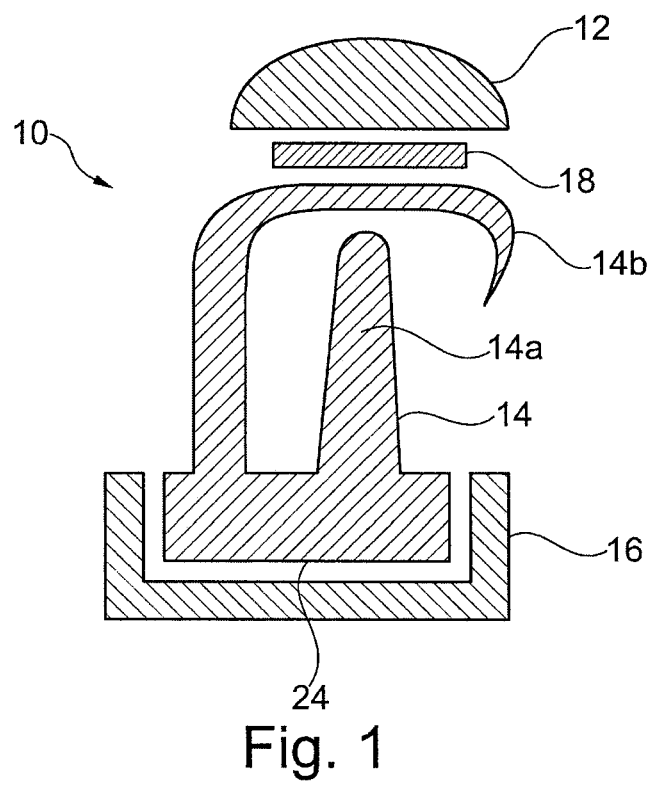

(51) Int. Cl.
| | |
|---|---|
| *B29C 43/40* | (2006.01) |
| *B29C 51/08* | (2006.01) |
| *B29C 43/02* | (2006.01) |
| *B29C 43/36* | (2006.01) |
| *B29L 31/00* | (2006.01) |
| *B29C 43/32* | (2006.01) |
| *B29K 75/00* | (2006.01) |

(52) U.S. Cl.
CPC .... *A61M 16/0616* (2014.02); *A61M 16/0622* (2014.02); *A61M 16/0688* (2014.02); *B29C 43/021* (2013.01); *B29C 43/203* (2013.01); *B29C 43/361* (2013.01); *B29C 43/40* (2013.01); *B29C 51/082* (2013.01); *A61M 16/0633* (2014.02); *A61M 2016/0661* (2013.01); *A61M 2207/00* (2013.01); *A61M 2210/0618* (2013.01); *B29C 2043/3255* (2013.01); *B29C 2043/3621* (2013.01); *B29K 2075/00* (2013.01); *B29L 2031/753* (2013.01)

(56) References Cited

U.S. PATENT DOCUMENTS

| | | | |
|---|---|---|---|
| 4,944,310 A | 7/1990 | Sullivan | |
| 5,647,357 A * | 7/1997 | Barnett | A61M 16/06 128/205.25 |
| 6,532,959 B1 | 3/2003 | Berthon-Jones | |
| 6,581,594 B1 | 6/2003 | Drew et al. | |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 2008/0047560 A1 | 2/2008 | Veliss et al. | |
| 2008/0060649 A1* | 3/2008 | Veliss | A61M 16/06 128/205.25 |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2010/0192955 A1 | 8/2010 | Biener et al. | |
| 2011/0005524 A1* | 1/2011 | Veliss | A61M 16/0666 128/206.24 |
| 2011/0088699 A1* | 4/2011 | Skipper | A61M 16/06 128/206.26 |
| 2011/0146684 A1* | 6/2011 | Wells | A61M 16/06 128/205.25 |
| 2011/0174310 A1* | 7/2011 | Burz | B29C 45/4407 128/206.24 |
| 2011/0253152 A1* | 10/2011 | Lin | D01F 1/10 128/849 |
| 2012/0055485 A1* | 3/2012 | Anthony | A61M 16/06 128/207.18 |
| 2012/0060843 A1* | 3/2012 | Magidson | A41D 13/1115 128/206.19 |
| 2012/0080035 A1* | 4/2012 | Guney | A61M 16/06 128/205.25 |
| 2012/0285455 A1* | 11/2012 | Varga | A61B 5/0836 128/204.21 |
| 2013/0139822 A1* | 6/2013 | Gibson | A61M 16/0683 128/205.25 |
| 2014/0109911 A1 | 4/2014 | Asvadi et al. | |
| 2014/0150799 A1* | 6/2014 | Daly | A61M 16/06 128/206.25 |
| 2014/0158136 A1 | 6/2014 | Romagnoli et al. | |
| 2014/0251338 A1* | 9/2014 | Asvadi | A61M 16/06 128/206.22 |
| 2015/0151066 A1* | 6/2015 | Chodkowski | A61M 16/06 128/206.24 |

FOREIGN PATENT DOCUMENTS

| | | |
|---|---|---|
| WO | WO 98/004310 A1 | 2/1998 |
| WO | WO 98/034665 A1 | 8/1998 |
| WO | WO 2000/078381 A1 | 12/2000 |
| WO | WO 03/016018 A1 | 2/2003 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 A1 | 2/2013 |

OTHER PUBLICATIONS

Written Opinion of the ISA for PCT/EP2015/063660, dated Sep. 29, 2015, 10 pages.

"*Respiratory Physiology*", by John B. West, Lippincott Williams & Wilkins, 9th edition published 2012 (8 pages).

* cited by examiner

SEAL FORMING STRUCTURE FOR A PATIENT INTERFACE AND A TOOL AND METHOD OF MANUFACTURING THE SEAL FORMING STRUCTURE

This application is the U.S. national phase of International Application No. PCT/EP2015/063660 filed 17 Jun. 2015, which designated the U.S. and claims priority to EP Patent Application No. 14172727.1 filed 17 Jun. 2014, the entire contents of each of which are hereby incorporated by reference.

2 BACKGROUND OF THE INVENTION

2.1 Field of the Invention

Forms of the present technology relate to a cushion assembly, particularly according to seal-forming structure and/or pad, a tool and/or a method of manufacturing at least part of a cushion assembly, preferably for use in a patient interface and also preferably for delivering a supply of pressurised air or breathable gas to an entrance of a patient's airways, particularly for providing ventilatory support for treatment of, e.g., Sleep Disordered Breathing (SDB).

2.2 Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Otherwise healthy individuals may take advantage of systems and devices to prevent respiratory disorders from arising.

2.2.1 Systems

One known product used for treating sleep disordered breathing is the S9 Sleep Therapy System, manufactured by ResMed.

Systems for treating SDB involve a blower which delivers a supply of air at positive pressure to a patient interface via a conduit. The patient interface may take several forms, such as a full face or nasal mask and patients are typically required to wear the mask for long periods, e.g., while sleeping, to receive, e.g., Noninvasive Positive Pressure Ventilation (NPPV) therapy.

The mask is typically held in place on a patient's head via a headgear arrangement. Masks typically comprise a rigid shell or frame and a soft face-contacting seal-forming structure, which may be a cushion. The seal-forming structure spaces the frame away from the patient's face and forms a seal with the patient's face as a result e.g. of its geometry, material and/or a contact force applied by the mask assembly, including mask and headgear arrangement.

A common problem with prior art devices is patient comfort. Patients can develop sores and red marks on their faces after several hours use of a mask. This may be due e.g. to excessive pressure that is applied to the wearer's face via the face contacting seal-forming structure which may result in discomfort and possibly skin irritation. In a further example this may, in addition or alternatively, be due to the seal-forming structure being distorted beyond its normal range of elasticity to conform to certain facial contours of the patient. Also, problems have been observed with regard to the patient interface appropriately conforming to the contour of a patient's face. This may result in leakage and/or the problems addressed above.

2.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) has been used to treat OHS, COPD, MD and Chest Wall disorders.

2.2.3 Patient Interface

The application of a supply of air at positive pressure to the entrance of the airways of a patient is facilitated by the use of a patient interface, such as a nasal mask, full-face mask or nasal pillows. A range of patient interface devices are known, however a number of them suffer from being one or more of obtrusive, aesthetically undesirable, poorly fitting, difficult to use and uncomfortable especially when worn for long periods of time or when a patient is unfamiliar with a system. Masks designed solely for aviators, as part of personal protection equipment or for the administration of anaesthetics may be tolerable for their original application, but nevertheless be undesirably uncomfortable to be worn for extended periods, for example, while sleeping.

2.2.3.1 Seal-Forming Portion

Patient interfaces typically include a seal-forming portion.

One type of seal-forming portion extends around the periphery of the patient interface, and is intended to seal against the user's face when force is applied to the patient interface with the seal-foaming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may leak. Furthermore, if the shape of the seal-forming portion does not match that of the patient, it may crease or buckle in use, giving rise to leaks.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

2.2.3.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

2.2.3.3 Vent Technologies

Some forms of patient interface systems may include a vent to allow the washout of exhaled carbon dioxide. Many such vents are noisy. Others may block in use and provide insufficient washout. Some vents may be disruptive of the sleep of a bed-partner 1100 of the patient 1000, e.g. through noise or focused airflow.

ResMed Limited has developed a number of improved mask vent technologies. See WO 1998/034,665; WO 2000/078,381; U.S. Pat. No. 6,581,594; US patent applications; US 2009/0050156; US Patent Application 2009/0044808.

2.2.3.4 Nasal Pillow Technologies

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063,328 and WO 2006/130,903 (describing amongst other things aspects of ResMed LIBERTY full-face mask); International Patent Application WO 2009/052,560 (describing amongst other things aspects of ResMed SWIFT FX nasal pillows).

2.2.4 PAP Device

The air at positive pressure is typically supplied to the airway of a patient by a PAP device such as a motor-driven blower. The outlet of the blower is connected via a flexible delivery conduit to a patient interface as described above.

3 BRIEF SUMMARY OF THE TECHNOLOGY

The following forms and aspects of the present technology are described and illustrated in conjunction with systems, tools and methods which are meant to be exemplary and illustrative, not limiting in scope.

The present technology is exemplary expressed by the features of the independent claims and aspects. The dependent claims and aspects refer to preferred embodiments. Additional and/or alternative features and aspects are discussed below.

One aspect of the present technology relates to providing a cushion assembly (or arrangement) for a patient interface (possibly a respiratory mask) for delivering a supply of pressurised air or breathable gas to an entrance of a patient's airways. The cushion assembly may comprise a seal-forming structure (possibly a cushion), also referred to as main cushion or main portion and/or a pad. Seal-forming structure and pad may be separately formed or, according to an alternative aspect of the present technology, integrally formed. The seal-forming structure comprises an inferior surface that may be a face contacting portion. The inferior surface faces a wearer's face in use and the seal-forming structure comprising a mask connection portion for connecting to a patient interface. The pad is preferably provided on the structure's inferior face and in some forms may be the only part of the cushion contacting the wearer's face. The pad comprises a surface for sealingly contacting a wearer's face in use. In this case, as stated above, the structure's inferior face, in use, does not itself contact the wearer's face but faces towards the wearer's face while the actual contact between wearer and cushion assembly is established by the pad. Alternatively, in use, the technology is designed such that the wearer's face is contacted by both, the structure's inferior surface and the pad's face contacting portion. Said inferior surface may thus also be referred to as face facing portion. The cushion assembly is connectable to a frame of the mask at a mask connection portion for connecting to a frame or shell of a patient interface. The connection portion is preferably provided at a side generally opposite the inferior surface.

Thus, in accordance with this aspect, the seal-forming structure may foam a three-dimensional geometry that may fulfill known geometrical, physical and/or operational functions relating to the fit of the seal-forming structure to the patient's face and to support a mask on a wearer's face in use.

The geometry of the pad, particularly when seen in relation to that of the seal-forming structure, may be referred to as "two-dimensional". Such "two-dimensional" geometry of the pad in one form of the present technology may mean that the pad has, e.g., a substantially flat and/or thin shape and/or a substantially constant thickness. If hypothetically observed in isolation spread on a flat surface, the pad may, in one form of the present technology, not include, e.g., any bulging regions. Alternatively, the pad may, while still having a substantially flat shape and/or a substantially constant thickness, be formed as a sheath or cover for being, e.g., pulled over a part of the seal-forming structure. Here, while imparting some kind of three-dimensionality when seen in isolation, e.g., that of a curved or non-flat plane, the pad still serves as a "two-dimensional" layer (or simply as a layer) on the seal-forming structure during use. Thus in these forms of the present technology the "two-dimensional" geometry of the pad does not affect the "three dimensional" geometry of the seal-forming structure and preferably only adds a thin layer, preferably of substantially constant thickness, on the seal-forming structure for interfacing between the seal-forming structure and the skin of the patient.

In one aspect of the present technology the pad is formed or comprises a foam material. Possibly, at least an outer side of the pad facing away from the seal-forming structure for contacting a wearer's face is flocked. By providing a flocked surface and serving as an interface between the seal-forming structure and a patient's face, the pad may be adapted to provide beneficial properties, e.g., as regards sealing effects, comfort to the patient and/or improved rigidity to the seal-forming structure, particularly due to it being flocked. By providing different quality categories of pad material by varying its parameters, e.g., such as thickness, resiliency, and/or flock, eventually in combination with different categories of structure or cushion softness or the like, comfort and/or feel to the patient may be influenced and particularly be improved.

Flocking may be understood to imply the provision of a plurality of fibers, filaments and/or threads, preferably attached to a base surface and, preferably, facing a patient's face during use. Such plurality of fibers, filaments and/or threads is hereafter described as a plurality of fibers, or simply as flocking. The plurality of fibers may extend away from said base surface. Preferably, the plurality of fibers is fixed to a base surface. The fibers may extend away from said base surface for contacting, preferably sealingly, a user's skin. The seal forming portion may improve the ventilation of the contact surface. The fibers may create a kind of slight, diffused leakage, preferably across the entire sealing surface. This diffused leakage may be perceived by users as a cooling, pleasant feeling, as opposed to a localized, punctual leakage often present in common patient interfaces using membranes, which is perceived as disturbing. Furthermore, the fiber length of the plurality of fibers may, in combination and in balance with the width of the contact surface and the sealing force applied by the sealing pad be specified such that a slight and diffused pleasant, cooling leakage perception is promoted, without drifting off into a too large leak rate which may otherwise be perceived as a poor seal. Moreover, the seal forming portion may improve the self-positioning of the patient interface, preferably in the nose region. This may be achieved, e.g., by a particular and preferred orientation of the fibers and/or by the lower coefficient of friction between fibers and the patient's skin, particularly compared to traditional silicone membranes. Silicone membranes, for instance, may have a tendency to adhere to the skin, so the user effectively has to lift the cushion off the skin and re-position it. Fibers may have a much lower tendency to adhere to the user's skin; therefore the mask cushion may be repositioned without removing it from the face, even during therapy.

Preferably, the plurality of fibers extends in the application position from the base surface towards the user's skin. The plurality of fibers may comprise a proximate end fixed to the base surface and a free distal end preferably adapted to be in contact with a user. Preferably, the plurality of fibers extends at an angle α of about 60°-120°, more preferably of about 75°-105°, and most preferably of about 90° from the base surface (in cases of doubt, preferably, from the tangent to the base surface). In other configurations the preferred angle may be about 45°. These angles refer to the unworn or unused state of the cushion while it will be understood that the orientation of the fibers may change when contacting or being pressed against a user's face. The plurality of fibers may be arranged substantially parallel to each other. The orientation of the plurality of fibers may also change in different regions of the interface or base surface. Alternatively or additionally, the fibers may be arranged at a density between about 10 to 100 g/m$^2$, preferably between about 20 and 65 g/m$^2$, and most preferably between about 30 and 45 g/m$^2$. The fibers may also be randomly oriented. Fibers may be made of viscose and/or polyamide. Viscose fibers may be arranged between about 10 and 50 g/m$^2$, more preferably between about 20 and 40 g/m$^2$, and most preferably between about 25 and 35 g/m$^2$. Polyamide fibers may be arranged at a density between about 25 and 65 g/m$^2$, more preferably between about 35 and 55 g/m$^2$, and most preferably between about 40 and 50 g/m$^2$. Alternatively or additionally, preferably, the fiber(s) has/have a length or height measured from the proximate end to the distal end of between about 0.01 and 5.0 mm, more preferably between about 0.05 and 2.0 mm and most preferably between about 0.1 and 1.0 mm. The fiber(s) may have a substantially round cross sectional shape. Alternatively or additionally, the fiber(s) may have a titre (yarn count) value [dtex] in a range of about 0.01 to 10 dtex, more preferably about 0.1 to 5 dtex, most preferably of about 0.5 to 2 dtex, wherein the Dtex is measured in g/10,000 m. The fiber(s) may be adapted to collapse, preferably in the application position and thus, when being pressed against a user's face. Preferably, the fibers simply bend away or buckle, rather than be compressed. The fiber(s) may predominantly tilt and/or bulge.

The fiber(s) may provide an adapted or controllable softness or resilience. Moreover, the sealing and/or ventilation as well as the sliding resistance may be adaptable/controllable by the variation of the above parameters of the fiber(s). By selecting the length, density, diameter, material and/or arrangement of the fiber(s), such as the orientation of the fiber(s), the properties of the seal forming portion may be adapted to a particular need. For instance, an open cell foam material may be provided with a seal forming portion providing airtight properties to the open cell foam which may reduce the risk of unintended leakage. The seal forming portion may be of a seal forming structure. The seal forming portion may form a perimeter arranged to surround an entrance to the airways of the patient so as to facilitate the supply of air at positive pressure to the airways. The patient interface preferably sealingly contacts a user's face. However a defined, diffused leakage at the seal forming portion located around the entire perimeter may amount to between 2 l/min and 60 l/min, preferably between about 5 l/min to 30 l/min.

In aspects of the present technology, the pad may be applied to the seal-forming structure by an adhesive with, e.g., an inner side of the pad comprising the adhesive. Alternatively, the pad may be removably laid or pulled over the seal-forming structure, e.g., as a cover or sheath. And further possibly the pad may be an integral part of the seal-forming structure.

In accordance with one aspect of the present technology there is also provided a method of manufacturing a seal-forming structure and/or pad, particularly for a patient interface for delivering a supply of pressurised air or breathable gas to an entrance of a patient's airways. The method may be adapted to manufacture a seal-forming structure and/or pad according to other forms of the technology. The method may comprise the steps of: providing a raw material, preferably a substantially flat sheet of raw material, and molding the raw material to form a molded, preferably three-dimensional, shape. Molding may be achieved by applying pressure and/or heat. The molded shape is preferably adapted to fit a patient's face in use. The raw material preferably comprises or is a foamed material, such as polyurethane or polyurethane ether foam (PU), silicone or silicone foam, or the like. Preferably, the raw material or sheet like raw material comprises a flocked surface on both its sides, or preferably one flocked surface, particularly for contacting a patient's face in use as a molded seal-forming structure or pad.

The molded product may be a seal-forming structure (possibly cushion) and/or pad as discussed above. If the molded product is a pad, it is particularly of the generally "two-dimensional" kind, as referred to above, which may still impart some kind of three-dimensionality when seen in isolation, as referred to above.

In one form of the present technology the pad may be formed integrally with the seal-forming structure during manufacturing. In other forms the pad may be placed on the molded shape of the manufactured seal-forming structure after manufacturing ended. This may be done at the manufacturing site, or later, e.g., by a distributor or seller or by the patient.

In one form of the present technology the method of manufacturing the seal-forming structure may include providing a tool, particularly a mold, comprising at least two tool or mold parts, locating the raw material between the two tool parts, and biasing at least one of the tool parts to close towards the other tool part to form the molded shape. In one form of the present technology, a respective tool is provided.

In forms of the present technology where the pad is non-integral with the molded shape, the pad may be placed at the outer, patient facing side of the molded seal-forming structure only after molding when the seal-forming structure assumed the shape adapted to fit a patient's face in use.

In forms of the present technology where the pad is integral with the molded shape, the raw material used in manufacturing may comprise or be the material of the pad, and the raw material may thus be shaped to form a structure with an integral pad for contacting the wearer's face during use. As already indicated above, in such form the seal-forming structure and pad are on part, wherein the seal-forming structure and pad may comprise or be made of the pad material as referred to above while having the structure's three-dimensional structure. This form of the present technology may combine the improvements of the seal-forming structure with those of the pad as well as with those of the manufacturing method.

The cushion assembly of the present technology may be adapted to be, preferably removably, connected to a frame of shell of a breathing mask. The frame or shell may be of a rigid structure, particularly being substantially more rigid than the cushion assembly.

The present technology may be of particular advantage in that it provides improved sealing characteristics and/or improved comfort characteristics thus improving patients' therapy compliance. Also, the quick, efficient and/or cost efficient manufacturing process allows provision of replaceable components such as pad and/or seal-forming structure. This may improve hygiene, patient comfort, and compliance. Furthermore, in embodiments where the pad may be placed onto an existing seal-foaming structure, such pads can serve as an optional upgrade to existing, e.g., silicone mask structures or cushions, particularly to improve the comfort by simply applying the, e.g., thermoformed, preferably foam, pad over the (silicone) structure or cushion by means of adhesive or by form factor.

Further additional and/or alternative forms and features of the present technology will be apparent from the following numbered aspects.

1. A cushion assembly for a patient interface for delivery of a supply of pressurised air or breathable gas to an entrance of a patient's airways, the cushion assembly comprising a seal-forming structure and a pad, the seal-forming structure comprising an inferior surface for facing a wearer's face when the patient interface is donned and a mask connection portion for connecting to a frame or shell of the patient interface, the pad being arranged on the inferior surface for sealingly contacting the wearer's face in use.

2. The cushion assembly according to aspect 1, wherein the pad is made of a foamed material and/or, wherein at least a portion of the pad is flocked, preferably wherein the portion of the pad for sealingly contacting a wearer's face is flocked.

2B. The cushion assembly according to aspect 1 or 2, the pad being the only part of the cushion assembly contacting the wearer's face when in use. In particular, in such embodiment, there is no membrane covering the pad.

3. The cushion assembly according to any one of the preceding aspects, wherein the pad is, preferably removably fixed to the seal forming structure, preferably by an adhesive, such as a pressure sensitive adhesive and/or wherein the pad is removably fixed to the seal forming structure and wherein the pad is in the form of a cover or sheath for being pulled over the seal forming structure.

4. The cushion assembly according to any one of the preceding aspects, the cushion assembly comprising a cushion element, and wherein, preferably, the pad comprises the cushion.

5. The cushion assembly according to any one of the preceding aspects, wherein the seal forming structure is connectable to the frame by an adhesive.

6. The cushion assembly according to any one of the preceding aspects, wherein the cushion and/or the seal forming structure comprises at least one of: a silicone material, a TPE material and/or an interior optionally filled, with a gel.

7. The cushion assembly according to any one of the preceding aspects, wherein the seal forming structure and/or pad comprises a foamed material, comprising at least one of polyurethane (PU), PUR, PVC, and wherein the seal forming structure and/or pad comprises a flocked surface portion, the flocking comprising at least one of viscose fibers, cotton fibers, Nylon, Polyamide and wherein the fibers are bonded to the pad material by an adhesive, comprising vinyl acetate or any other solvent-free adhesive.

8. The cushion assembly according to any one of the preceding aspects, wherein at least portions of both the inferior surface and the pad contact the wearer's face in use.

9. The cushion assembly according to any one of the preceding aspects, wherein the seal forming structure comprises a membrane for supporting forming a seal with a wearer's face during use.

10. A method of manufacturing a pad and/or seal forming structure for a patient interface for delivery of a supply of pressurised air or breathable gas to an entrance of a patients airways, according to the cushion assembly according to any one of the preceding aspects, the method comprising the steps of:
providing a raw material, in a substantially flat condition and
molding the raw material, using pressure and/or heat, to form a desired three-dimensional shape, adapted to fit a patient's face in use.

11. The method according to aspect 10, further including the steps of:
providing a tool comprising at least two mold parts, locating the raw material between the two mold parts, and positioning at least one of the mold parts to close towards the other mold part to form the molded shape, and including the step of providing heat to at least one, preferably both, of the mold parts and thus the material to be molded.

12. The method according to aspect 10 or 11, wherein the raw material is the material described in aspect 2 and/or 7.
13. The method according to any one of aspects 10 to 12, wherein the raw material comprises a flocked surface, the raw material being arranged such in the mold that the flocked surface of the molded shape forms a surface for contacting a wearer during use.
13B. The method according to any one of aspects 10 to 13, wherein the raw material is a flat sheet like material.
13C. The method according to any one of aspects 10 to 13B, wherein the raw material has a thickness of about 5 to 40 mm, preferably of about 5 to 20 mm, more preferably 10 to 25 mm, and most preferably between 12 and 20 mm. These ranges are of particular advantage, preferably both as regards comfort and manufacturability. If the material is too thin, for example, the effect of thermoforming as discussed herein cannot be readily accomplished. If the material is too thick, for example and on the other hand, controlled molding or thermoforming is no longer possible.
13D. The method according to any one of aspects 10 to 13C, wherein the raw material is a foam material one side of which, preferably two opposing sides of which, is/are flocked.
14. The method according to any one of aspects 10 to 13, wherein one of the mold parts comprises a cavity for forming the molded shape and the raw material is located between the two mold parts with the surface for forming a surface for contacting a wearer during use facing the cavity.
15. The method according to any one of aspects 10 to 14, wherein the raw material is inserted into the mold in a first relative position of the mold parts and wherein, after insertion of the raw material, the mold parts are moved towards one another until a second relative position is reached, and wherein, in the second relative position, the material is molded to the desired shape and/or wherein the mold parts are positioned in a third relative position such that the molded shape is separated from excess raw material, and wherein in the third relative position the formed pad and/or seal-forming structure is fully contained in the cavity.
16. The method according to any one of aspects 10 to 15, wherein one of the mold parts comprises a cavity and wherein the molded shape is formed by raw material that is urged into the cavity, wherein the shape of the cavity assists in providing the desired shape to the raw material during molding.
17. The method according to any one of aspects 10 to 16, wherein the mold comprises at least one, two or more, positioning members, which are adapted to position the two mold parts in the second relative position upon closing and/or to allow the mold parts to take the third relative position.
18. The method according to any one of aspects 10 to 17, wherein the raw material is heated and wherein heating induces the raw material in the cavity to at least partially take the shape of the cavity.
19. The method according to any one of aspects 10 to 18, wherein upon moving of the mold parts from the second relative position to the third relative position the molded shape is separated from excess raw material located outside of the cavity.
20. The method according to any one of aspects 10 to 19, wherein the cavity comprises a shallow segment and a deep segment, such that a part of the molded shape formed by the shallow segment forms a membrane or sealing lip and/or such that a part of the molded shape formed by the deep segment forms a seal forming structure and/or pad.
21. The method according to aspect 20, wherein at least at one point during formation of the molded shape compression forces within the shallow segment are larger than within the deep segment.
22. The method according to any one of aspects 10 to 21, wherein at least one of the mold parts comprises at least one cutting edge for separating excess raw material from the shaped material, and wherein separation between the molded shape and excess raw material is at least partially accomplished by the at least one cutting edge.
23. The method according to any one of aspects 10 to 22, wherein at the second relative position the at least one cutting edge does not engage the raw material.
24. The method according to any one of aspects 10 to 23, wherein the at least one cutting edge is formed at the intersection of two surfaces, wherein an angle between the two surfaces forming the cutting edge is an obtuse angle, a straight angle, or an acute angle.
25. The method according to any one of aspects 10 to 24, wherein the cutting edge is formed on one mold part and, in the closed, third relative position of the mold, the at least one cutting edge is located in a recess formed in another mold part not comprising the at least one cutting edge.
26. The method according to any one of aspects 10 to 25, wherein at least one of the mold parts comprises an insert for shaping the raw material, the insert comprising a shaping geometry, comprising the cavity.
27. The method according to any one of aspects 10 to 26, wherein the mold part comprising the insert and the insert each comprise a leading side facing an opposing mold part, wherein the cavity is provided on the leading side of the insert, the insert being movable between an extended state where the leading side of the insert projects above the leading side of the respective mold part and a retreated state where the leading side of the insert is located at or below to the leading side of the respective mold part.
28. The method according to aspect 27, wherein when the mold parts are at the second relative position the insert is at the extended state.
29. The method according to any one of aspects 10 to 28, wherein at least one of the mold parts further comprises at least one stop movable between an extended state where the stop projects above a leading side of the tool part facing another mold part, and a retracted state where the stop is at or below the leading side of the mold part.
30. The method according to aspect 29, wherein when the mold parts are at the second relative position the stop is at the extended state.
31. The method according to any one of aspects 10 to 30, wherein the tool comprises opening means for urging the mold parts to take the first relative position, i.e. an extended state.
32. Mold for forming at least part of a cushion assembly according to any one of the preceding cushion assembly aspects and/or for performing a method according to any one of the preceding method aspects, the mold comprising at least a first and a second mold part for molding a raw material to a desired shape.

33. A tool for manufacturing a seal forming structure and comprising at least two mold parts, preferably according to any one of aspects 11 to 32, wherein one of the mold parts comprises a cavity for forming a molded shape that opens in a given direction at a rim towards the other mold part.
34. The tool according to aspect 33, wherein the cavity comprises a shallow segment and a deep segment as viewed along the given direction.
35. The tool according to aspects 33 or 34, wherein at least one of the mold parts comprises at least one cutting edge that is adapted to delimit at least a portion of the rim of the cavity.
36. The tool according to aspect 35, wherein the at least one cutting edge is formed at the intersection of two surfaces, wherein an angle between the two surfaces forming the cutting edge is an obtuse angle, a straight angle, or an acute angle.
37. The tool according to aspects 35 or 36, wherein the mold part not comprising the cutting edge comprises a recess that is adapted to receive the cutting edge.
38. The tool according to any one of aspects 33 to 37, wherein at least one of the mold parts comprises an insert and wherein the insert comprises the cavity.
39. The tool according to aspect 38, wherein the mold part comprising the insert and the insert each comprise a leading side facing the other mold part, wherein the cavity is provided on the leading side of the insert, the insert being movable between an extended state where the leading side of the insert projects above the leading side of the respective mold part and a retreated state where the leading side of the insert is located at or below to the leading side of the respective mold part.
40. The tool according to aspect 39, wherein at least one of the mold parts further comprises at least one stop movable between an extended state where the stop projects above a leading side of the tool part facing the other mold part, and a retracted state where the stop is at or below the leading side of the mold part.
41. Kit, comprising a cushion assembly according to any one of aspects 1 to 9, including at least two, preferably three or more, pads, wherein the pads preferably have differing parameters.
42. Kit according to aspect 41, the parameters including geometry and/or material and/or surface quality.
43. Kit according to aspect 42, the parameters include thickness, flock, resiliency, and/or softness.

In addition to the exemplary aspects and embodiments described above, further aspects and embodiments will become apparent by reference to the figures and by study of the following detailed descriptions.

Other features of the technology will be apparent from consideration of the information contained in the following detailed description, abstract, drawings and claims.

4 BRIEF DESCRIPTION OF THE SEVERAL VIEWS OF THE DRAWINGS

Figure 2:
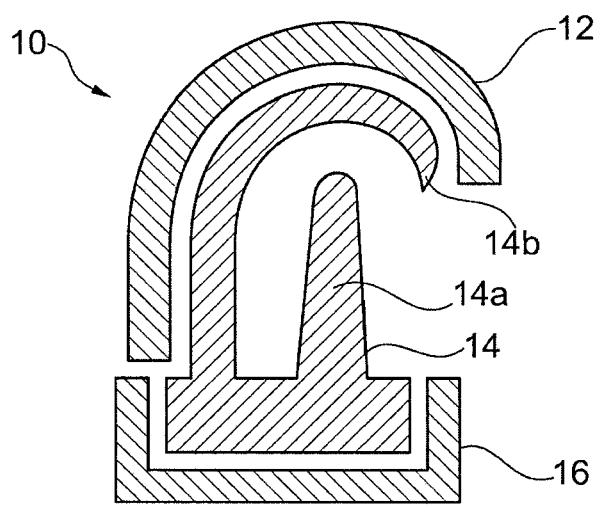
Figure 3A:
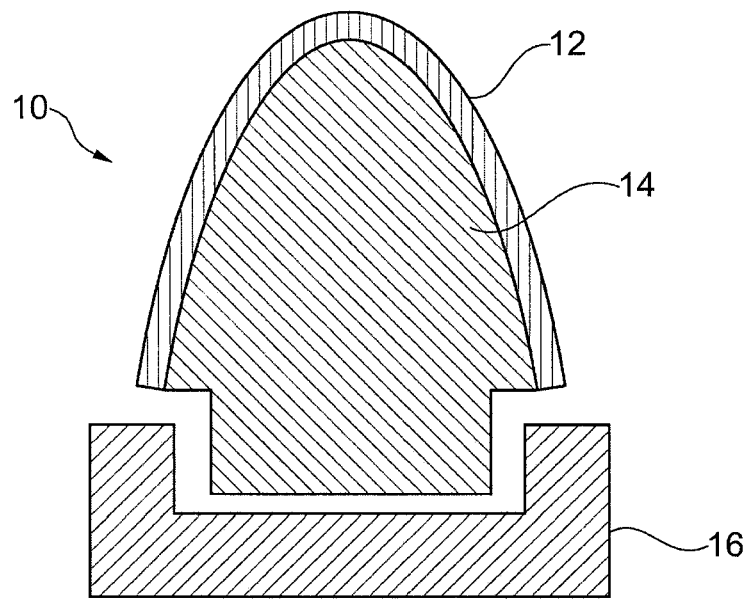
Figure 3B:
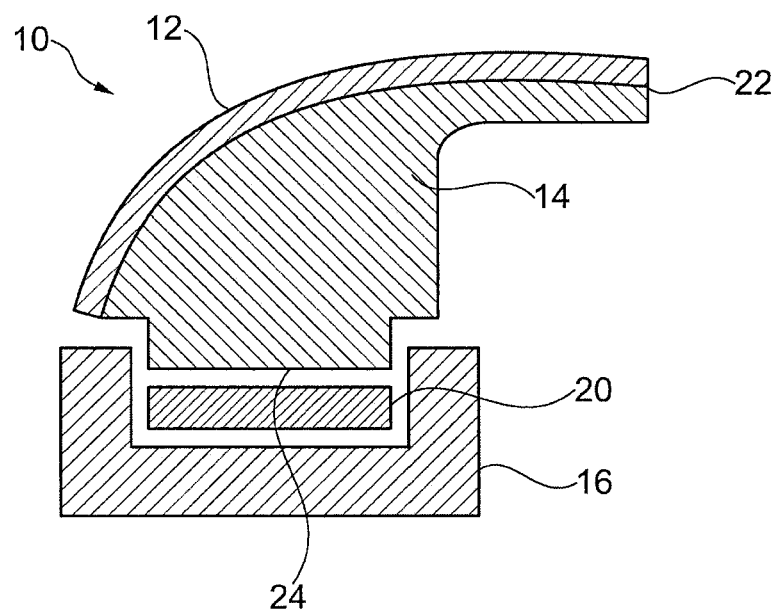
Figure 8A:
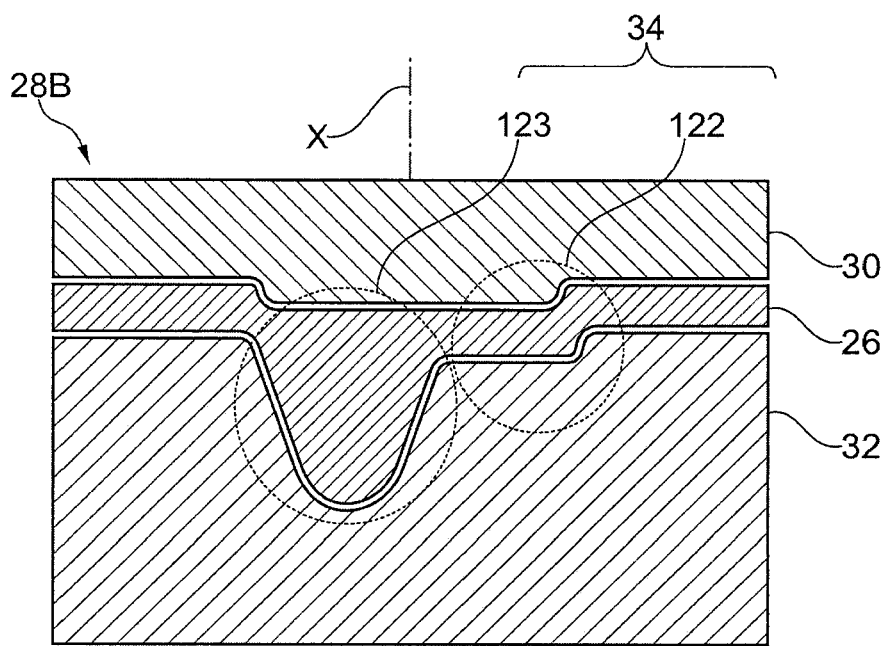
Figure 8B:
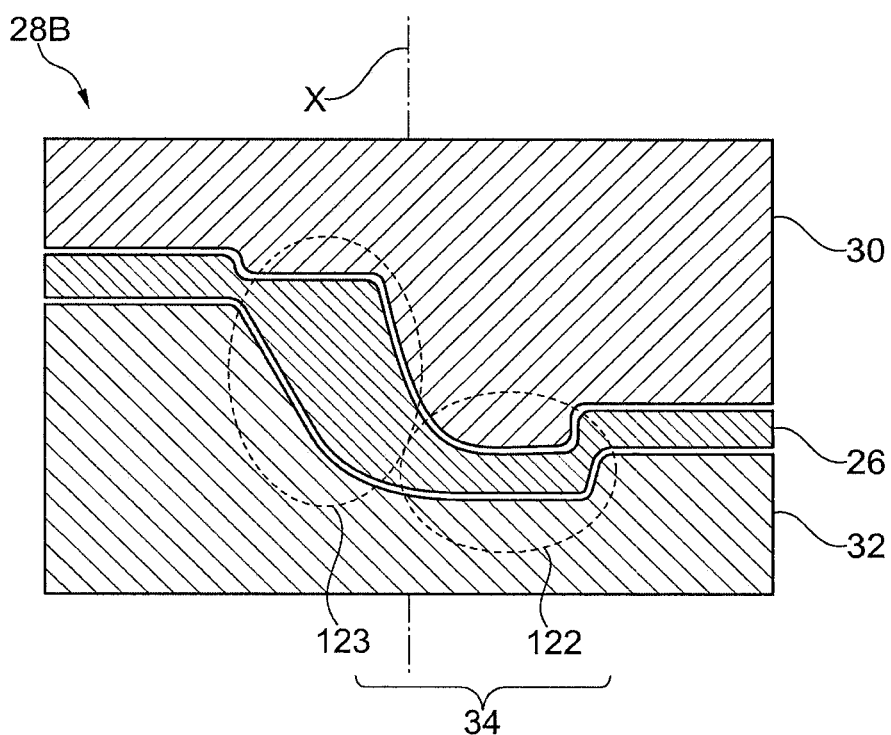
Figure 8C:
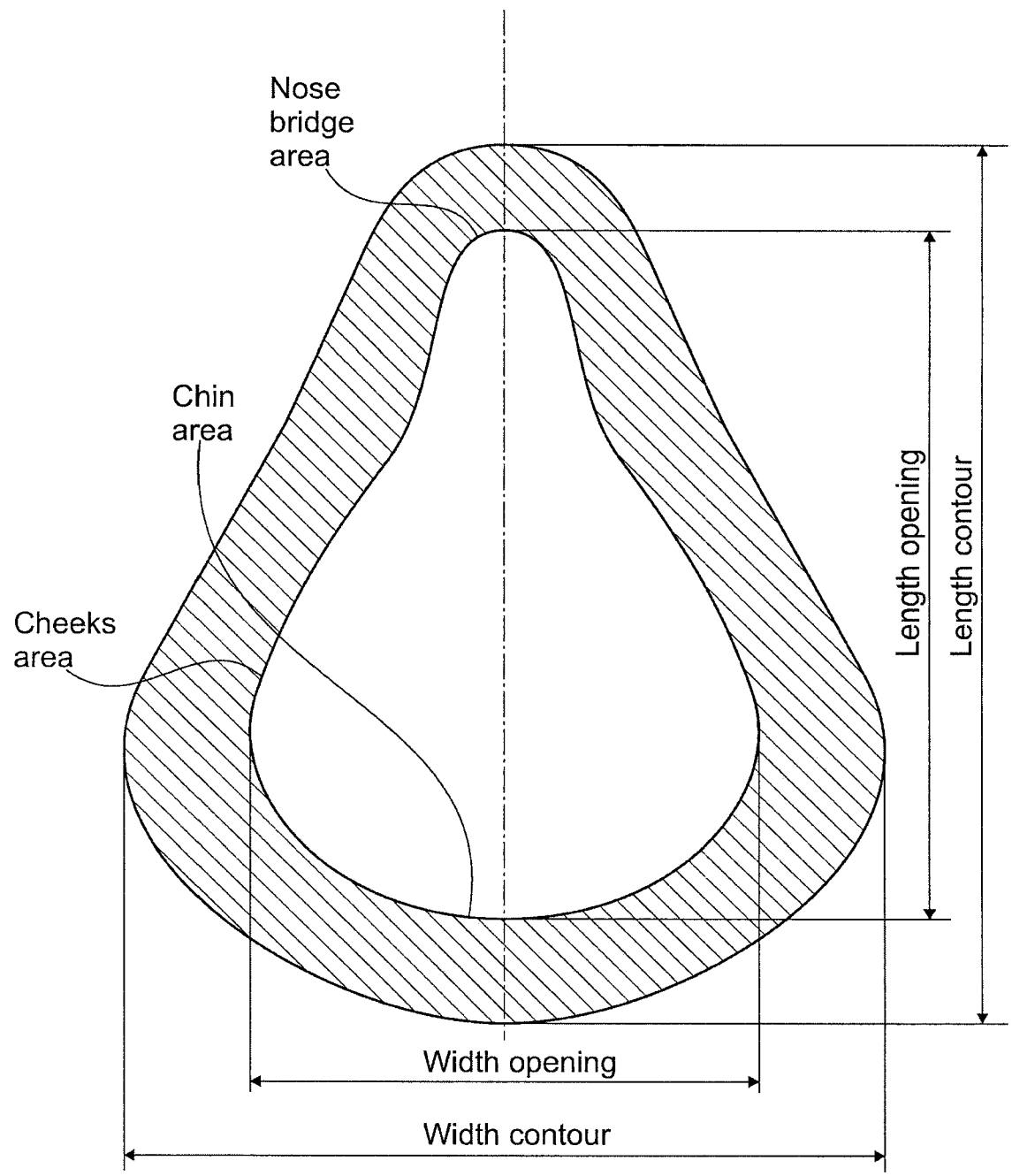
Figure 10:
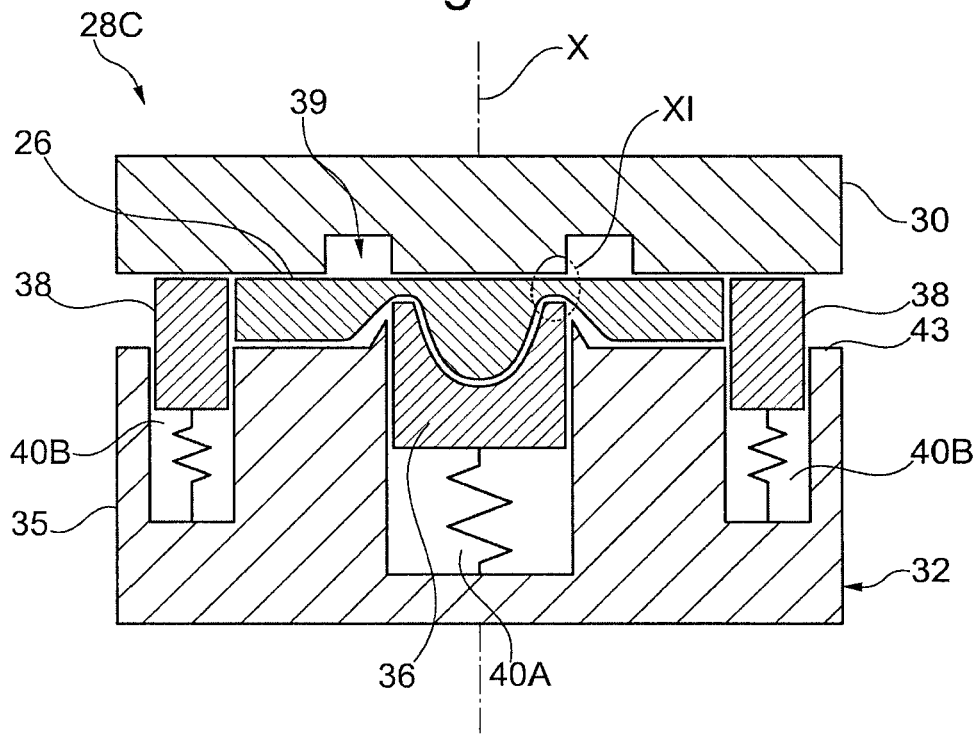
Figure 11:
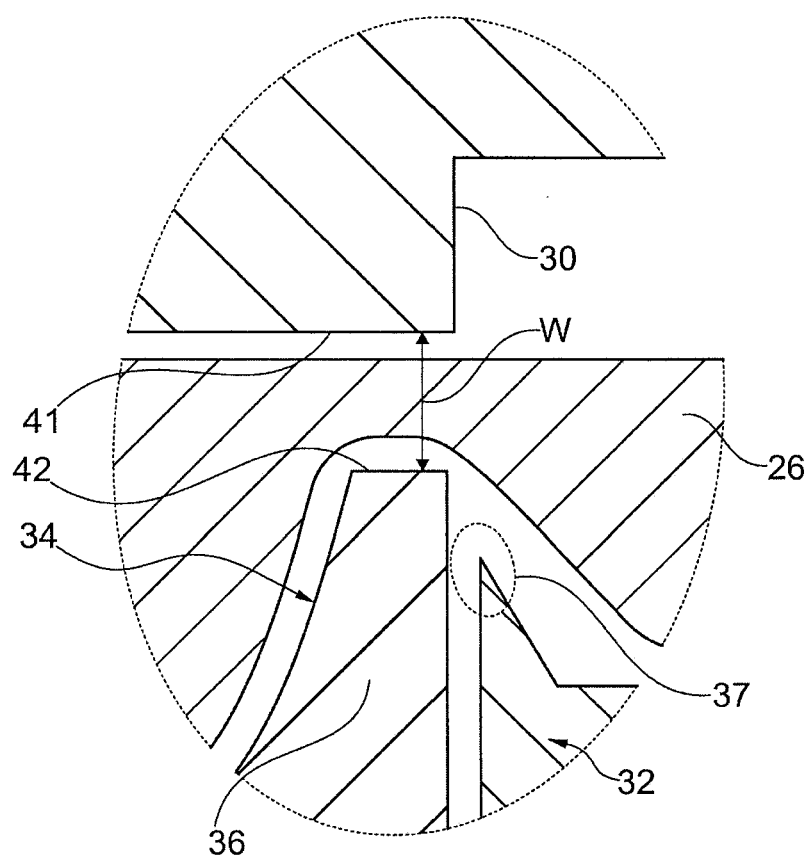
Figure 12:
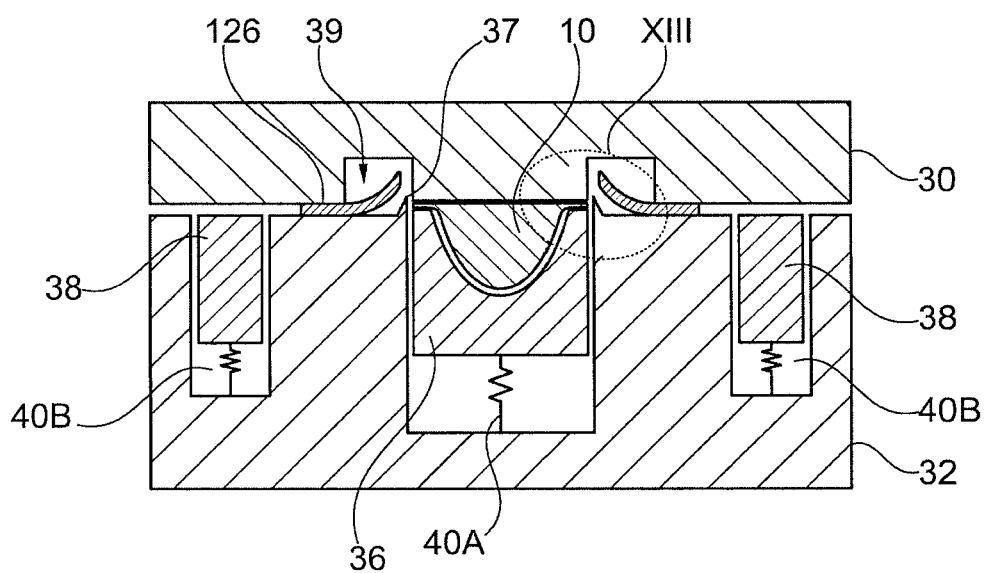
Figure 13:
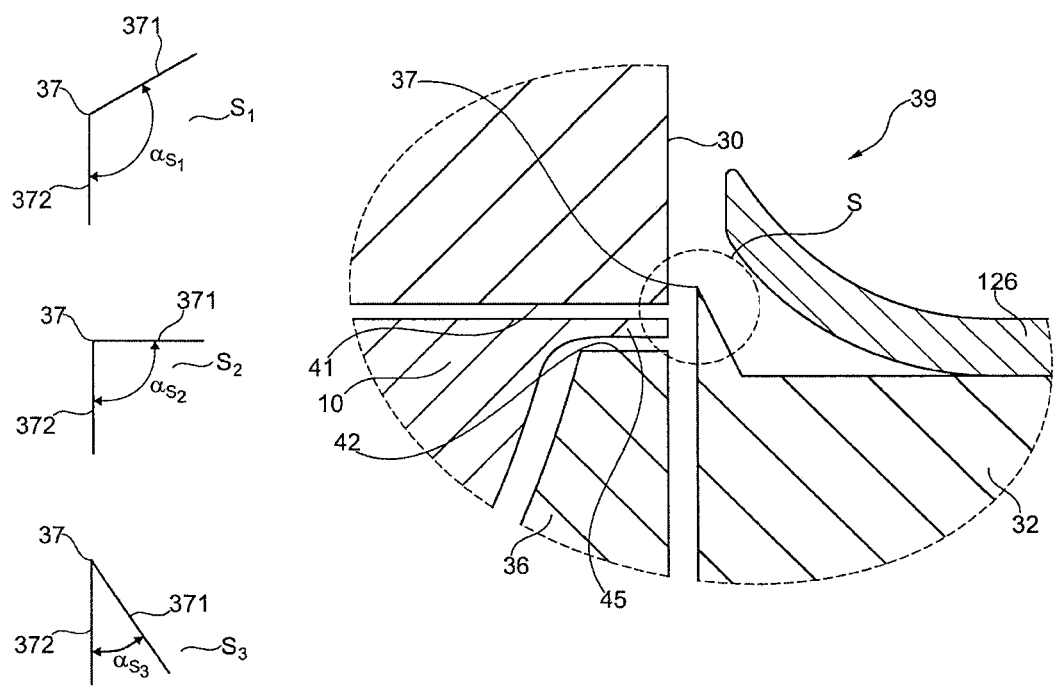

The present technology is illustrated by way of example, and not by way of limitation, in the figures of the accompanying drawings, in which like reference numerals refer to similar elements including:

Exemplary embodiments are illustrated in referenced figures. It is intended that the embodiments and figures disclosed herein are to be considered illustrative, rather than restrictive. The technology, however, both as to organization and method of operation, together with objects, features, and advantages thereof, may best be understood by reference to the following detailed description when read with the accompanying figures, in which:

FIG. 1 schematically shows a cushion assembly in accordance with one form of the present technology;

FIG. 2 schematically shows a cushion assembly in accordance with another form of the present technology;

FIGS. 3A and 3B schematically show cushion assembly s in accordance with yet a further form of the present technology;

FIGS. 4 to 7 schematically show a tool and/or method for forming at least part of a cushion assembly in accordance with one form of the present technology;

FIGS. 8A and 8B schematically show a tool and/or method for forming at least part of a cushion assembly in accordance with another form of the present technology;

FIG. 8C schematically shows a cross section of a cushion assembly in accordance with some forms of the present technology;

FIGS. 9 to 12 schematically show a tool and/or method for forming at least part of a cushion assembly in accordance with yet a further form of the present technology; and FIG. 13 schematically shows an enlarged section of item XIII in FIG. 12.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated within the figures to indicate like elements. It will well be understood that features shown and discussed with regard to a form of the present technology may well be used with and applied to another form of the present technology, unless technically impossible or otherwise stated herein.

5 DETAILED DESCRIPTION OF EXAMPLES OF THE TECHNOLOGY

Masks used for providing breathable gas to a patient in accordance with the various forms of the preset technology include a cushion assembly. In the following description various forms of cushions will be described including tools and/or methods for forming such cushion assembly s.

FIG. 1 shows a cushion assembly or assembly 10 in accordance with one form of the present technology. The cushion assembly 10 includes a pad 12 (also referred to as an "add-on" pad), preferably made of a foamed material, that is placed onto a seal-forming structure, possibly a cushion 14 of the cushion assembly. The structure 14 has a base portion or mask connection portion 24, here at an opposite side to where pad 12 is located. Cushion assembly 10 may be attached via base 24 to a frame or shell 16 of a mask (only a schematic connection portion of frame or shell 16 of the mask is shown), preferably a breathing mask for treating sleep disordered breathing, e.g., by CPAP therapy or the like. The form of the cushion assembly here shown has a double-walled construction comprising an under seal-forming structure (or undercushion) 14a and a membrane 14b. The membrane preferably at least partly extends over the under structure or cushion 14a, and preferably, provides an inferior surface constituting a face contacting or face facing portion of the seal-forming structure. However other known forms of cushion assembly's, e.g. not comprising a membrane, may be applied in accordance with the present technology.

In one form of the present technology the connection between pad 12 and the seal-forming structure 14 may be realized by providing an adhesive 18. The adhesive may be applied to pad 12 during manufacturing of the pad so that, e.g., an end user may adhere the pad 12 to the main portion himself/herself, including replacement of a worn down or used pad 12. The pad 12 in accordance with various forms of the present technology may have a simple, two-dimensional, preferably flat geometry. Here, all functions relating to the fitting of the mask to the face contour of the patient may be fulfilled by the three dimensional geometry of the seal-forming structure 14.

Attention is drawn to FIG. 2 schematically showing one form of the present technology where an "add-on" pad 12 may serve as a cover or case that is placed over the seal-forming structure 14. Here, again, although the pad 12 may be understood to impart some kind of three-dimensionality, it if formed as a thin, sheet or layer like material that provides a layer over the seal-forming structure 14. Preferably such that the seal-forming structure 14 is formed with and provides a three-dimensional geometry for achieving the functional characteristics for supporting a mask on the patient's face and for proper adaptation of the seal-forming structure to the patient's general physiognomy. The form of the cushion assembly here shown also has a double-walled construction comprising an under structure or cushion 14a and a membrane 14b. However other known forms of cushion assemblies may be applied in accordance with the present technology. Since pad 12 here optionally serves as a cover, use of an adhesive may not be necessary for attaching pad 12 to seal-forming structure 14. Pad 12 when used as a cover may be attached to main portion 14 (here membrane 14b) by e.g. being stretched over the main portion and held in place by form fit, eventually supported by the pad's elasticity.

Attention is drawn to FIGS. 3A and 3B where in one form cushion assembly 10 is seen optionally attached to mask frame 16 in a conventional manner (FIG. 3A), e.g., using mechanical connection means. In another form, cushion assembly 10 is seen optionally attached to frame 16 by means of an adhesive 20 (FIG. 3B). Preferably the adhesive 20 may be applied to base 24 of the cushion assembly during manufacturing so that the end user may adhere cushion assembly 10 himself/herself to the mask. The seal-forming structure 14 of these two forms of cushion assembly may have (as in previous foul's of the present technology) a complex three-dimensional geometry required for fitting to a patient's face. As can be seen in FIGS. 3A and 3B, cushion assembly 10 may comprise a seal-forming structure 14 and an "add on" pad 12, as referred to above. However, in other forms of the present technology (e.g., as discussed in the following paragraphs) pad 12 may be a flocked portion of a foamed seal-forming structure 14 so as to form an integrally formed "flocked foam cushion" assembly 10.

A preferred idea of this technology is to have a patient interface made of flocked foam material. As indicated above, in FIG. 3, 14 may indicate the foam while 12 may indicate the flocking layer on top of the foam—the flocking layer is not shown in FIGS. 1 and 2 to simplify the drawing, but is preferred to be also present in the technologies shown in these Fig's as well. Unlike in the previous Fig's, in FIGS. 3A and B there is preferably no "mask cushion" to which the foam is applied, rather, the foam itself comprises or constitutes the mask cushion. The manufacturing method and tool described below nevertheless are preferably suitable to produce both types of (foam) patient interface: the "flocked (foam) cushion" (as shown, e.g., in FIGS. 3A, B) and the "add-on (foam) pad" (as shown, e.g., in FIGS. 1, 2). This aspect is understood to be also covered by the discussion in the below paragraph.

Accordingly, cushion assembly 10 seen, e.g., in FIGS. 3A and 3B may comprise a seal-forming structure with an integrally formed pad, or in other words, a pad with an integrally formed seal-forming structure. In the following, no distinction will be made between these two alternatives while the reference numerals referring to either of them may individually refer to all alternatives. In one form, as seen, e.g., in FIG. 3B, the seal-forming structure 14 may be provided e.g. with a lip or membrane structure 22, particularly in order to improve the sealing effect on the face of the patient. The membrane 22 may be formed of the seal-forming structure 14 and/or pad 12.

The seal-forming structure 14 of the various forms of cushion assembly's 10 in accordance with the present technology may be made of: silicone, thermoplastic elastomeric (TPE) material, PU material, foamed material and/or may include interior cavities filled other substances such as gel. In accordance with various forms of the present technology pad 12 in its preferably foamed structure may also be flocked at its face contacting side, preferably. This may allow for provision of different quality categories of, e.g., foam pads 12 to various forms of cushions 10. As shown in FIG. 3, pad 12 may be directly formed on seal-forming structure 14, e.g., by means of flocking.

Figure 4:
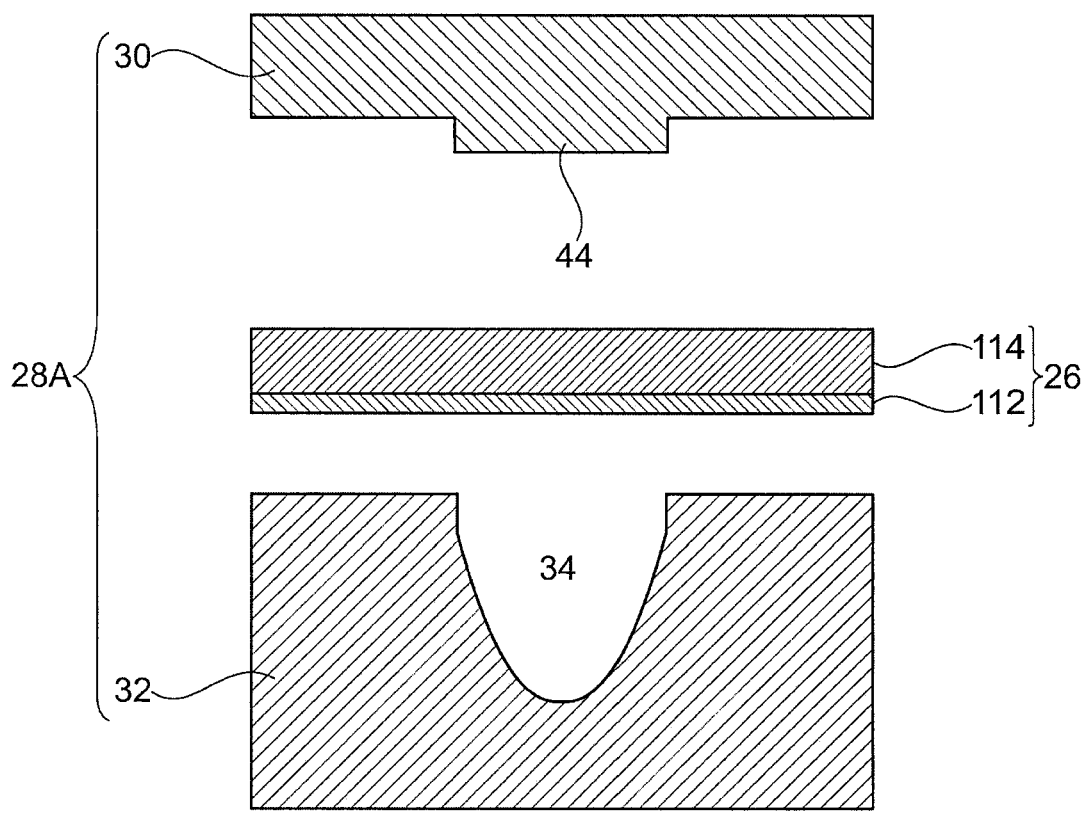

Attention is drawn to FIG. 4. In accordance with one aspect of the present technology, at least some forms of the cushion assembly's 10 or of the structures 14 or pads 12 may be manufactured in a forming process (preferably a thermoforming manufacturing process) from a raw material 26.

Preferably, aspects of the present technology relate to a manufacturing method (preferably including "Thermoforming") for shaping a flocked foam material. The shaping may turn the raw material a) into a foam pad, which can be applied basically to any existing mask, OR b) into a mask cushion.

According to a preferred aspect, the raw material 26 comprises or consists of a foam material (e.g., 14 in FIG. 3, 114 in FIG. 7) to which a flocking layer (e.g., 12 in FIG. 2, 112 in FIG. 7) is applied. This flocking layer may be advantageous for the thermoforming process, as it may protect the foam from being, e.g., scorched by the hot tool half (see, e.g., 32 in FIG. 7). In trials with non-flocked foam, this behavior was indeed observed, leading to, e.g., unsightly appearance, comfort restrictions, and unpleasant odour.

In point (a) above, the (thermoformed) flocked foam pad is intended simply as an "add-on" to, e.g., make existing masks more comfortable. Point (b) above refers to an idea of "obsolescing" the traditional (silicone) cushion entirely by replacing it, preferably with a cushion consisting of thermoformed flocked foam.

In forms where cushion assembly 10 (i.e. seal-forming structure 14 and pad 12) is integrally formed in the manufacturing process, one raw material 26 may be used. Alternatively, raw material 26 may be used for manufacturing a pad 12 for covering part of a seal-forming structure, where the cushion to which the pad is applied may be a traditional mask cushion, e.g. made of silicone.

Raw material 26 may preferably be provided in a flat, sheet like manner. It may include a base material 114 which is provided with a specific surface quality on one side, e.g., with a flocked surface 112 as seen in FIG. 4; however in an embodiment (not seen) the specific surface quality e.g. with flocked surface 112 may be provided at both sides of base material 114 thus sandwiching base material 114 therebetween. As indicated above, in one form of the present technology, raw material 26 consists of or comprises a foam material 114 to which a flocking layer 112 is applied (see, e.g., FIG. 7). In addition, in some forms of the present technology, flocking layer (of flocked surface) 112 may serve in the thermoforming process, to also protect the foam of base material 114 from being scorched by a hot tool part (such as e.g. mold part 32 seen in FIG. 7).

In some forms of the present technology, raw material 26 may be shaped in the thermoforming process into a foam pad (either flocked or non-flocked), which may then be applied to any existing mask as an "add-on" to make existing masks more comfortable.

In a first step of one form of a manufacturing process, a raw material (e.g. 26) may be inserted into a tool or mold 28A including first and second mold parts 30, 32. When placing raw material 26 in the tool, in forms of material 26 including surface 112, this surface 112 is preferably oriented such that it faces into a direction that is intended, in use of the seal-forming structure, to face out of the manufactured cushion assembly 10, i.e., towards the patient's face. This allows, in use of the product, said surface to at least partially contact the patient's face. One of the tool parts, here 32, may include a cavity 34 for forming the shape of the cushion assembly 10 (or, as stated above, pad 14 or integrally formed pad and seal-forming structure, eventually also referred to as cushion assembly 10). In forms of the present technology this cavity may define the direction that is intended to face out of the manufactured cushion assembly 10, i.e., to face towards a patient's face in use. Consequently, in these forms, raw material 26 may be placed in tool 28A with, preferably flocked, surface 112 facing towards cavity 34. As shown, while cavity 34 is provided in one mold part 32, the second, opposing mold part 30 may be provided with a protrusion 44, particularly for urging raw material 26 into cavity 34 and thus molding raw material to take a desired shape. Preferably, at least one of the tool parts 30, 32 may be heated.

Figure 5:
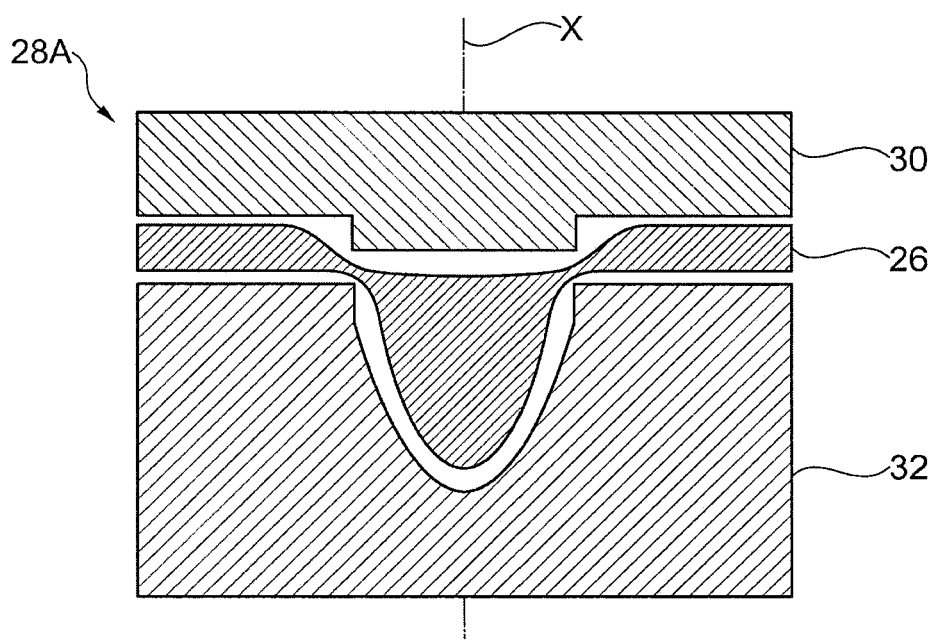

With attention drawn to FIG. 5, a further possible step of the manufacturing process is seen in which tool 28A (or a portion of tool 28A, such as mold part 32 and/or mold part 30) moves along an axis X to a partially closed position. In other words, mold parts 32, 30 move from an open position relative to one another (as seen in FIG. 4), also referred to as first relative position, towards one another to take a more closed, or second relative position (as seen in FIG. 5). This may be accomplished by moving first part 30 towards second part 32 and/or second part 32 towards first part 30. In the partially closed second relative position, raw material 26 may be physically urged into cavity 34 by protrusion 44 and the closing distance or gap (preferably extending along axis X, preferably the closing direction) between parts 30 and 32. As can be seen in FIG. 5, while some of the raw material 26 is urged into the cavity, remainders of raw material extend outwardly (in the FIG. towards the right and left) from the cavity, eventually while still being physically connected to the part of material urged into the cavity. Here, it may be of advantage that the second relative position of the mold parts does allow raw material to be urged and/or to be drawn from between the mold parts 30, 32 into the cavity. Preferably, having a "partly closed" position before moving the tool into the fully closed position contributes to achieving a "flow" of material from between the mold halves into the cavity 34. In keeping the tool in such semi-closed position, the material can be allowed time sufficient to take shape during the thermoforming process, before then cutting off excess material as the tool moves into the closed position. This may assist in providing a large coverage of flocking layer on the outer surface, as deformation potentially occurring during thermoforming can be (partly) compensated by additional material being drawn into the cavity.

At the partially closed position tool 28A rests for a defined period of time, while at least in this position, tool 28A or at least part of the tool in a vicinity adjacent cavity 34 may be heated so that raw material 26 urged into cavity 34 may be molded to assume and take the shape of the cavity.

Time required for thermoforming the material may in some forms mainly depend on the material grade used, and on the material thickness. In one from, based on from experimental trials, the duration may be between about 1 and 6 minutes, and preferably around 3 minutes, for a polyurethane foam material of 20 mm base material thickness. For substantially thinner base materials, a thermoforming duration of less than about one minute may be conceivable, while for substantially thicker base materials thermoforming duration of more than 6 minutes may be required.

Figure 6:
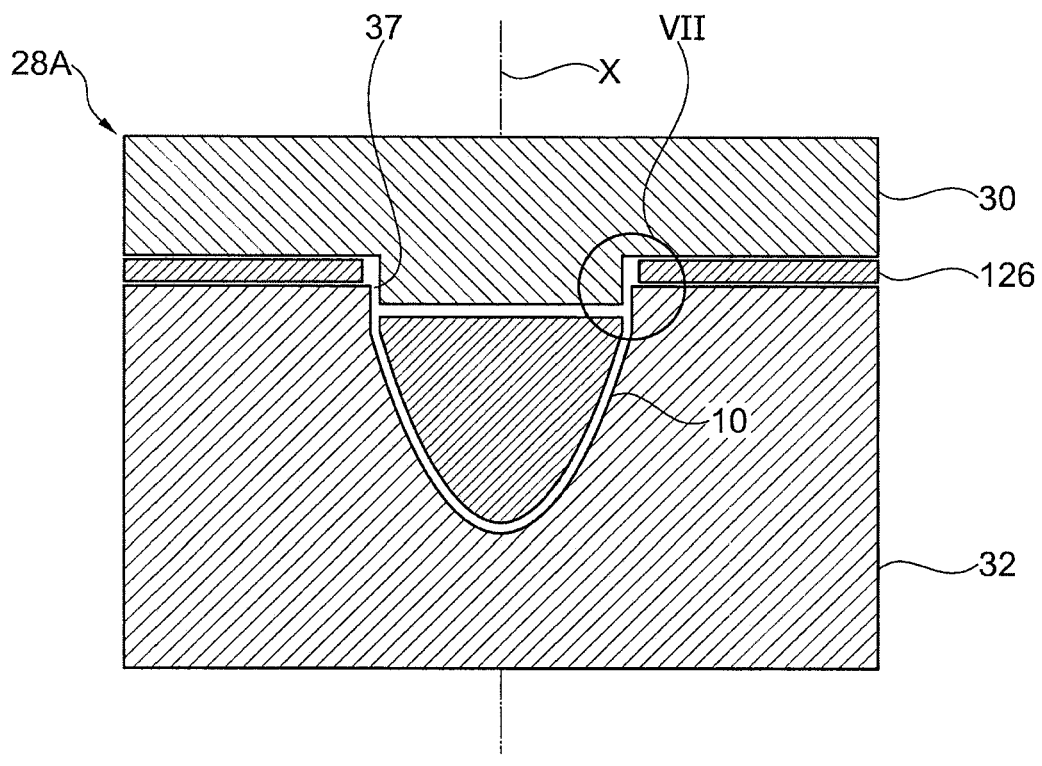

After the defined period of time passed and the raw material 26 has been at least partially shaped, the tool may move to a completely closed or third relative position seen in FIG. 6. This may be accomplished by moving first part 30 towards second part 32 and/or second part 32 towards first part 30. In some embodiments, the time it takes to move from the open position seen in FIG. 4 to the partially closed position seen in FIG. 5 is (i.e. including the "defined period of time" where tool 28A rests at the partial closed position); is substantially longer than the time it takes to move from the partially closed position seen in FIG. 5 to the closed position seen in FIG. 6. The time for which the tool remains in the partial closed position seen in FIG. 5 is in the space of several seconds to several minutes depending on material properties and temperatures.

In the closed third relative position of mold parts 30, 32, cutting edges 37, which may advantageously be provided, e.g., on one of mold part 30, 32, separate the shaped part of the raw material from excess raw material 126 that is not used or required for forming the cushion assembly (seal-forming structure and/or pad). The excess raw material 126 may be the raw martial 26 not contained in cavity 34 in the closed third relative position of the mold parts. The cutting edges may thus be arranged such, preferably in the vicinity of the cavity, that the molded product has the desired shape.

Figure 7:
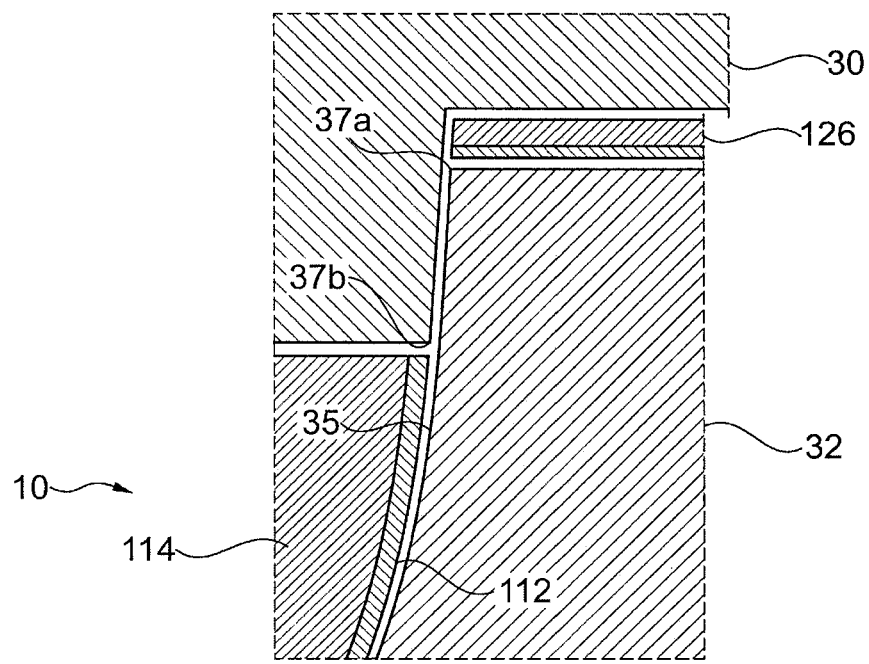

In the detail drawing shown in FIG. 7, one possible form of a cutting edge 37a is seen in an enlarged view of detail VII indicated in FIG. 6. Cutting edge 37a may additionally or alternatively be provided as cutting edge 37b on mold part 30, preferably on protrusion 44. Also in this view it is seen that surface 112, after molding, is completely provided on the outer and patient facing side of the seal-forming structure that is adapted for contacting the patient in use. This may be accomplished, as seen in FIG. 7, by a manufacturing process in which in the final or third position of tool 28A, after cutting off any excess raw material, cushion assembly 10 contacts an inner face 35 of cavity 34 only via surface 112. In forms of cushion assembly 10 where surface 112 is a flocked surface, this may result in cushion assembly 10 being completely enclosed or formed by the flocked foamed material of pad 12. Here, seal-forming structure 14 may be considered concealed by, i.e., integrally formed with or by pad 12.

Exemplary summarizing the above, the tool may move from open position FIG. 4 to a closed position FIG. 6, via reaching a transitory position FIG. 5 along the way. While it progresses from the position shown in FIG. 4 to that shown in FIG. 5, material is urged into the cavity, and consequently some more of the raw material is drawn into the mould cavity 34. The tool may then rest in the partly closed position for a certain time, preferably until the foam assumes the softening temperature required for thermoforming. Consequently, the foam may then assume the shape of the cavity. After a defined time period, the tool may then move into the fully closed position shown in FIG. 6. In doing so, the tool preferably shears off remaining raw material to produce the moulded part.

Attention is now drawn to FIGS. 8A and 8B showing possible forms of tools 28B and its mold parts configured for manufacturing optional structures in cushion assembly 10 (in the seal-forming structure 14 and/or pad 12). These structures may typically be used for assisting in contact, fit and/or for aid in contact or fit of a cushion assembly to a patient's face in use. These structures may be in the form of a membrane (such as membrane 14B in FIG. 2) and/or sealing lip (such as lip 22 seen in FIG. 3B) or any other three dimensional structure fitted for contacting or aiding in contacting and/or fitting the patient's face. In both FIGS. 8A and 8B, tool 28B is seen after movement along axis X to its partial closed second relative position of the mold parts. In FIG. 8A cavity 34 is seen optionally formed mainly in the second part 32 of tool 28B, and in FIG. 8B cavity 34 is seen formed partially in the first part 30 and partially in the second part 32 of the tool. In addition, in both FIGS. 8A and 8B cavity 34 is seen optionally including of a shallow segment 122 and a deep segment 123.

The shallow segment 122 may be defined by a portion of the cavity that has a small relative distance along axis X between the first and second mold parts 30, 32 in the closed third relative position of the mold parts of tool 28B. The deep segment 123 may be defined as a portion of the cavity that has a large relative distance along axis X between the first and second parts 30, 32 in the closed third position of tool 28B. In the shallow segment of cavity 34 a relatively long flattened area of the cushion assembly 10 may be shaped, eventually due to the strong compression forces exhibited in this segment during the manufacturing process. Tool 28B as seen in FIG. 8A can be realized so that the shallow segment 122 may be shaped at the side of a final cushion assembly that may be adapted to attach a frame of the mask. Or, tool 28B as seen in FIG. 8B can be realized so that the shallow segment 122 may be shaped at the side of a final cushion assembly that may be adapted to contact, fit and/or be closer to the patient's face in use.

In a non-binding example, cushion assembly 10 may be characterized in some form is of the present technology by one or more of the following technical data:

The material of pad 12 may include: polyurethane ether foam (PU foam).

Pad 12 in its preferably foamed structure may have a foamed density according to ISO845 of: about 44+/−2 kg/m$^3$.

Pad 12 in its preferably foamed structure may have hardness i.e. compression hardness 40% according to ISO3386 of: about 2.2+/−0.35 kPa.

The tensile strength of pad 12 according to ISO1798 may be: ≥ about 80 kPa.

The elongation of pad 12 at break according to ISO1798 may be: ≥ about 200%.

Pad 12 in its preferably foamed structure may have a cell size from about 500 to about 730 μm.

In forms of the present technology in which pad 12 may be flocked, the flocked material of pad 12 may include viscose fibers with a fiber length of about 0.2 to about 0.3 mm.

Materials such as vinyl acetate may be used for adhesive binding of pad 12 to seal-forming structure 14 and/or of seal-forming structure 14 to frame 16.

Starting thickness of the foamed material of pad 12 may be from about 5 to about 50 mm, and in some forms of the present technology also thicker materials may be conceivable. The starting thickness may depend on the final geometry to be achieved—for example, a seal-forming structure as that seen in FIG. 2 may need a rather thin starting material, a seal-forming structure according that seen in FIG. 3A may need a rather thick starting material, and a seal-forming structure according to that seen in FIG. 1 may require a starting thickness of about 5 to about 20 mm.

In some forms of the present technology, particularly with seal-forming structure and pad being integrally formed, the final thickness of cushion assembly 10 after manufacturing may depend on its geometry. In the cushion seen in FIG. 1 the final thickness may be between about 5 to about 10 mm, in the cushion seen in FIG. 2 the final thickness may be between about 2 to about 5 mm, and in the cushion seen e.g. in FIG. 3A the final thickness may be between about 10 to about 40 mm, wherein the additional membrane 22 may be in the range of about 0.5 to about 20 mm. The same thicknesses also apply to the pad of the present technology alone. Such pad thickness may be determined without any additional cushion structure.

The pad may be provided with a maximum pad thickness between about thickness of about 5 to 40 mm, preferably of about 5 to 20 mm, more preferably 10 to 25 mm, and most preferably between 12 and 20 mm. These ranges are of particular advantage, preferably both as regards comfort and manufacturability. If the material is too thin, for example, the effect of thermoforming as discussed herein cannot be readily accomplished. If the material is too thick, for example and on the other hand, controlled molding or thermoforming is no longer possible. The pad thickness may vary along the perimeter and/or width of the pad. Moreover, the pad thickness may vary in a direction perpendicular to the direction of extension along the perimeter. The average thickness of the pad may vary between about +/−75%, preferably between about +/−50% of the average thickness of the pad measured in the direction C. The seal forming portion may be curved in a cross-sectional view (i.e. in a view perpendicular to the extension of the pad along the perimeter; cf. FIG. 8a, 8b). The pad may thus have, in a cross-sectional view, an at least two-dimensional shape. The shape of such a pad may also be called a 2.5D shape. The pad may be a substantially flat material with a bulge or a curve in the patient contacting portion. Such a pad may be easy to manufacture by punching or cutting out of a sheet material as further described below. The thickness of the pad, as referred to above, is preferably substantially the same as the thickness of an underlying cushion structure, as discussed further herein.

With attention drawn to FIG. 8C, the length/width of the mask cushion assembly after processing will be addressed. In an embodiment, the length/width may be in the range of:

Length from chin area to nose bridge area about 70+/−30 mm at an inner "length opening" (l-o) as well as about 120+/−30 mm at an outer "length contour" (l-c). Width of cheek area from left to right about 60+/−30 mm at an inner "width opening" (w-o) as well as about 90+/−30 mm at an outer "width contour" (w-c).

The above dimensions may in some forms represent a largest extent of a dimension present in a cushion assembly according to an embodiment of the present technology. The dimensions may be measured at points with horizontal tangents to the curve in case of "width", and vertical tangents to the curve in case of "length". The dimensions may vary with different forms of the present technology, depending on the actual shape of the geometry, whether used for a full face or nasal mask, whether the foam is formed as a pad or a seal-forming structure, whether or not a sealing lip is present etc. Means of measurement, of the above dimensions may be provided by optical measurement devices, so as not to deform the elastic part during metrology. Horizontal and vertical as used above refers to respective orientations as seen in FIG. 8C with the shown orientation of a seal-forming structure, which generally exhibits a somewhat triangular shape in a top view (e.g. onto the face contacting side or vice versa).

Figure 9:
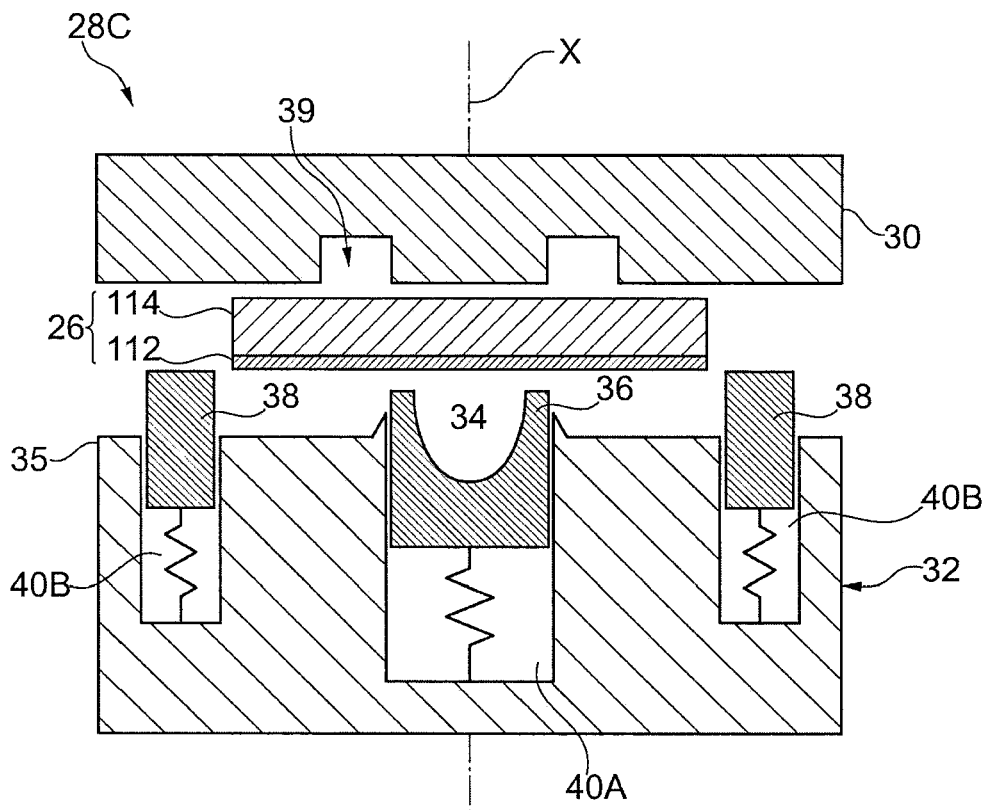

Attention is now drawn to FIG. 9 showing a further form of a tool 28C in accordance with the present technology. Here tool 28C comprises a first part 30 in the optional form of a pressure plate and a second part 32 optionally constituting a mold side of the tool. The second part 32 includes a body 35, one or more stops or positioning members 38 and an insert 36 possibly including a cavity 34 for generally defining the shape of the cushion to be formed during manufacturing. The positioning members 38 and the insert 36 may be movable relative to the body 35 or mold part 32 and their movement and/or position relative to the body may be realized by passive and/or active biasing means 40A, 40B coupled to insert 36 and positioning members 38, respectively. Passive biasing means may be realized by passive elements such as springs, gas pressure dampers or a mechanical coupling to the pressure plate. Active biasing means may be realized by actors such as, e.g., electrical drives, pneumatic or hydraulic cylinders or the like. These can be set to withstand a predefined load or force in order to allow the mold parts to take, e.g., the desired first, second and third relative positions.

In manufacturing, raw material 26 may be inserted between the first and second parts 30, 32 when tool 28C in its open, first state seen in FIG. 9. Raw material 26 may be inserted into tool 28C, if applicable with a surface 112 facing into a direction that is intended to be an inferior surface or face contacting portion of the manufactured cushion. This direction in tool 28C may be defined by part 32 that includes cavity 34 (directly in mold part 32 or indirectly via insert 36, as further discussed below) so that surface 112 in the manufactured cushion may be at a side that contacts/fits the patients face in use. Although in tool 28C, entities defining the patient-side geometry (e.g. insert 36, cavity 34) are formed in second part 32 in other forms of the present technology these entities may in addition/alternatively be realized (similar to e.g. cavity in FIG. 8B) in first part 30 possibly forming the pressure plate side.

After positioning raw material 26 in tool 28C, the tool may be moved to its partially closed, second position seen in FIG. 10. In this position the stops 38 may be configured such that they withstand a first closing force $F_{S1}$ of the tool 28C that urges tool 28C to close towards its partial closed position. In some forms of the present technology, the first closing force $F_{S1}$ of tool 28C may be generated by common methods, such as hydraulic and/or pneumatic methods. Also electrical and/or or mechanical methods may be implemented in other forms of the present technology.

The stops 38 thus may guarantee in some forms of the present technology that tool 28C may not move beyond a second position necessary for shaping raw material 26 by resisting the first closing force $F_{S1}$. One possible view of tool 28C in its partial closed second position can be seen in FIG. 11 which is an enlarged section of FIG. 10. The biasing means 40A defining/urging insert 36 away from body 35 and against mold part 30, may be realized to allow the raw material 26 to be compressed to a width W (along axis X). Width W may depend on the thickness of the raw material 26 at its starting position before being compressed and may typically lie in the range of 0.5 mm to 10 mm. Width W is measured along axis X between a leading side 41 of first part 30 facing insert 36, and a leading side 42 of cavity 34 which also constitutes a leading side of insert 36 proximal to the first part 30. Preferably, width W corresponds to the raw materials thickness in a most compressed position.

At the partial closed second position, tool 28C (or at least a portion of tool 28C adjacent cavity 34) may be heated to a shaping temperature $T_A$. The shaping temperature $T_A$ may be realized by common methods, such as by introducing electrical solid body heaters or heated gases or liquids, or by high-energy radiation such as infrared radiation. Further possibilities of forming the shaping temperature may be realized by energy generated by e.g. oscillations, for example by ultrasound, or by kinetic energy, generated by e.g. impact energy.

In some forms of the present technology, it may be feasible to heat both sides of the tool to possibly a similar or the same temperature, which may have an advantage of providing e.g. for a faster cycle time. In other forms of the present technology, it may be desirable to heat mainly or exclusively the "cavity" side (e.g. second part 32) of the tool, thereby achieving a "cold" tool part (e.g. first part 30) capable of supporting and conveying the raw material, and a "hot" tool part (e.g. 32) for thermoforming the desired shape, which may be advantageous in easier conveying of the raw material (less stress during thermoforming), and in a more easily controllable process.

Heating may include the entire tool or entire cavity side, or may be localized close to the shape of the cavity, e.g. by cooling channels (not seen). Heating through such channels may be advantageous where temperature cycles are needed, e.g. switch from lower "insertion" temperature to higher "thermoforming" temperature, and then back to "lower" demoulding temperature.

In an embodiment temperature $T_A$ may cycle between preferably two temperature limits. The lower limit may be present when the tool is fully opened (as e.g. in FIG. 4) or fully closed (as e.g. in FIG. 6), to facilitate demoulding of the thermoformed part and feeding of fresh raw material. The upper temperature limit may be present in the semi-closed position (as e.g. in FIG. 5), as the foam assumes the intended shape in the thermoforming process. In some forms of the present technology, for the purpose of cooling the tool, a means of heat dissipation may be present in addition to the heating, e.g. a fan and heat sink, cooling fluids etc. In addition, in some forms of the present technology, for the purpose of energy efficiency and faster cycle time, ideally only the parts of the tool directly involved in shaping the raw material during thermoforming may be heated, and this may then require a form of thermal insulation between the heated and un-heated parts of the tool.

In one form of the present technology, tool 28C includes cutting edges 37 that in the partial closed second position of tool 28C are positioned such that they do not engage the raw material 26. In FIG. 11 one form of implementing this non engagement may be seen by cutting edge 37 being positioned axially trailing below the leading side 42 of cavity 34 and insert 36 (with the 'below' direction being defined as a direction away from the first part 30).

After expiry of the shaping time $T_4$, tool 28C may be moved into a completely closed third position by increasing the closing force to a second closing force $F_{S2}$. The second closing force $F_{S2}$ may be configured to be sufficient to overcome the forces applied by biasing means 40B that maintain the stops 38 at extended positions relative to a leading side 43 of the body 35 that faces first part 30. In forms of the present technology in which the biasing means 40B are implemented as active means (such as: actors, electrical drives etc.), such means 40B may be activated to retreat the stops 38 back into to a received position in body 38 in order to clear the way for the closing tool 28C.

Attention is drawn to FIG. 12 showing one form of tool 28C in (or towards) its completely closed third position. As tool 28C reaches the completely closed third position, the cutting edge/edges 37 cut and separate the raw material 26 into, e.g. two, pieces. A first piece being the molded part in cavity 34 constituting cushion assembly 10 or the seal-forming structure 14 or pad 12. A second piece being the excess raw material 126 left outside of cavity 34 and/or outside and beyond the cutting edges 37 at a region distal from the cavity 34.

In FIG. 13 which is an enlarged section of item XIII in FIG. 12 this separation made by cutting edges 37 can be seen in greater detail. Here it can also be seen that tool 28C in some forms of the present technology may include recesses 39 (see, e.g., FIG. 12) for receiving the cutting edges 37 in the final closed position of the tool. In this form of tool 28C, recess 39 may be provided in the first part of the tool so that cutting edge 37 may enter the recess and cut the raw material 26 in a manner resembling a punching device. As seen in FIG. 13, in some forms of the present technology, cushion assembly 10 may be provided with a welded edge 45 that may be formed by spring loaded insert 36 giving way (i.e. being urged away from part 30) in the closed state of tool 28C to the material that is compressed between sides 41 and 42.

In the completely closed position, the tool possibly clamps a portion of the material adjacent to an area where edge 37 cuts, to avoid tearing during the "cutting" step. The flocking layer (e.g. 112 in FIG. 7) in some forms may not cover the entire perimeter, such as along the plane of cutting of e.g. the "welded" edge created through compression in combination with temperature. "Welded" edge 45 in some forms may assist in preventing compressed foam from expanding and exposing its non-flocked interior. A welded edge may particularly be advantageous in case two layers of flocking (e.g. layer 112 in FIG. 7) are present on either side of base material (e.g. 114 in FIG. 7). Welding such two flocking layers together may in some forms of the present technology cause the base material (e.g. 114) to be completely enclosed in the flocking layer, to achieve e.g. air and water tightness of the foam pad. However, a partly exposed foam layer that may exist in some forms of the present technology in this area may possibly be shaped or positioned in a seal-forming structure so that the face contacting portion during use may be the flocking layer. In some forms, the foam base material which may be biocompatible, like the flocking layer, may also contact the patients face in use. A width of leading side 42 (seen e.g. in FIG. 11) may be optimized to achieve sufficient welding effect with minimal width and in some forms may be between about 1 and 2 mm.

The encircled section 'S' in FIG. 13 surrounds the cutting edge 37 of tool 28C and at the left side of FIG. 13 various optional forms of structural designs of cutting edge 37 are illustrated. As seen, cutting edge 37 may be defined as being formed at an intersection where two surfaces 371, 372 meet, and in a plane perpendicularly passing though a given point along the cutting edge 37 an angle α between the two surfaces 371, 372 adjacent the given point may be: obtuse (section S1), straight (section S2), or acute (section S3).

In various forms of tool 28C, such as those here shown, elements such as the insert 36, stops 38 and cutting edge 37 may be implemented on the second part 32 of tool 28C which optionally constitutes the mold part. However, in other forms of the present technology (not shown) it may be possible to house one, more or all of these elements in any combination in the first part 30 of the tool that optionally constitutes the pressure plate of the tool. In addition it is noted that while cutting edge 37 has been shown in tool 28C to be body 35 in a modified tool 28C cutting edge 37 may be located on insert 36 so that possibly a cushion 10 produced by such a modified tool would not have a welded edge 45.

While the technology has been illustrated and described in detail in the drawings and foregoing description, such illustration and description are to be considered illustrative or exemplary and non-restrictive; the technology is thus not limited to the disclosed embodiments. Variations to the disclosed embodiments can be understood and effected by those skilled in the art and practicing the claimed technology, from a study of the drawings, the technology, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures can not be used to advantage. The present technology is also understood to encompass the exact terms, features, numerical values or ranges etc., if in here such terms, features, numerical values or ranges etc. are referred to in connection with terms such as "about, ca., substantially, generally, at least" etc. In other words, "about 3" shall also comprise "3" or "substantially perpendicular" shall also comprise "perpendicular". Any reference signs in the claims should not be considered as limiting the scope.

The invention claimed is:

1. A cushion assembly for a patient interface for delivery of a supply of pressurized air or breathable gas to an entrance of a patient's airways, the cushion assembly comprising a seal-forming structure and a pad, the seal-forming structure comprising an inferior surface for facing a wearer's face when the patient interface is donned and a mask connection portion for connecting to a frame or shell of the patient interface, the pad being arranged on the inferior surface for sealingly contacting the wearer's face in use, wherein the pad is made of foamed material comprising a flocked surface portion having a plurality of fibers, each of the fibers having a length that promotes gas leakage through the flocked surface portions, wherein:

the pad being the only part of the cushion assembly contacting the wearer's face when in use, and each of the fibers has a free distal end adapted to contact the wearer's face and a proximal end fixed directly to the inferior surface.

2. The cushion assembly according to claim 1, wherein only part of the pad includes the flocked surface portion.

3. The cushion assembly according to claim 1, wherein the pad is removably fixed to the seal forming structure by an adhesive, and wherein the pad is in the form of a cover or sheath for being pulled over the seal forming structure.

4. The cushion assembly according to claim 1, the cushion assembly comprising a cushion element, wherein the pad comprises the cushion element.

5. The cushion assembly according to claim 1, wherein the seal forming structure comprises at least one of: a silicone material, and/or a thermoplastic elastomeric (TPE) material.

6. The cushion assembly according to claim 1, wherein the seal forming structure comprises a foamed material, comprising at least one of polyurethane (PU or PUR) or polyvinyl chloride (PVC), and wherein the seal forming structure comprises a flocked surface portion, the flocked surface portion of the seal forming structure comprising fibers, Nylon, and/or Polyamide bonded to the pad by an adhesive comprising vinyl acetate or any other solvent-free adhesive.

7. The cushion assembly according to claim 1, wherein the seal forming structure comprises a membrane for supporting forming a seal with a wearer's face during use.

8. A method of manufacturing the cushion assembly of claim 1, the method comprising:
forming the pad and/or seal-forming structure by:
providing a raw material, in a substantially flat condition and
molding the raw material, using pressure and/or heat, to form a desired three-dimensional shape, adapted to fit a patient's face in use.

9. The method according to claim 8, further including:
providing a tool comprising at least two mold parts,
locating the raw material between the two mold parts, and
positioning at least one of the mold parts to close towards the other mold part to form the molded shape,
and including providing heat to at least one of the mold parts and thus the material to be molded.

10. The method according to claim 9, wherein the raw material is inserted in a first relative position of the mold parts and wherein, after insertion of the raw material, the mold parts are moved towards one another until a second relative position is reached, and wherein, in the second relative position, the material is molded to the desired shape and/or wherein the mold parts are positioned in a third relative position such that the molded shape is separated from excess raw material, and wherein in the third relative position the formed pad and/or seal-forming structure is fully contained in the cavity.

11. The method according to claim 9, wherein one of the mold parts comprises a cavity and wherein the molded shape is formed by raw material that is urged into the cavity, wherein the shape of the cavity assists in providing the desired shape to the raw material during molding.

12. The method according to claim 9, wherein upon moving of the mold parts from the second relative position to the third relative position the molded shape is separated from excess raw material located outside of the cavity.

13. The method according to claim 8, wherein the raw material comprises a flocked surface, the raw material being arranged such in the mold that the flocked surface of the molded shape forms a surface for contacting a wearer during use.

14. The cushion assembly according to claim 1, wherein the seal forming structure comprises an interior filled with gel.

15. The cushion assembly according to claim 1, wherein the length of the fibers is between about 0.01 and about 5.00 mm.

16. The cushion assembly according to claim 15, wherein the length of the fibers is between about 0.1 and about 1.0 mm.

17. The cushion assembly according to claim 1, wherein the fibers have a titre value of about 0.01 to about 10 dtex, wherein dtex is measured in g/10,000 m.

18. The cushion assembly according to claim 1, wherein the flocked surface portion is configured to promote gas leakage in the range of about 2 l/min to about 60 l/min.

19. The cushion assembly according to claim 1, wherein the fibers extend at an angle of about 45° relative to a base surface to which the fibers are fixed, when not worn by the wearer.

20. The cushion assembly according to claim 1, wherein the fibers are arranged at a density of about 20 g/m$^2$ to about 60 g/m$^2$.

21. A cushion assembly for a patient interface for delivery of a supply of pressurized air or breathable gas to an entrance of a patient's airways,
the cushion assembly comprising a seal-forming structure and a pad, the seal-forming structure comprising an inferior surface for facing a wearer's face when the patient interface is donned and a mask connection portion for connecting to a frame or shell of the patient interface,
the pad being arranged on the inferior surface for sealingly contacting the wearer's face in use, wherein the pad is made of foamed material comprising a flocked surface portion having a plurality of fibers, each of the fibers having a length that promotes gas leakage through the flocked surface portions, wherein
the pad being the only part of the cushion assembly contacting the wearer's face when in use, and
wherein the fibers extend at an angle of about 60° to about 120° relative to a base surface to which the fibers are fixed.

* * * * *